(12) United States Patent
Ahari

(10) Patent No.: US 12,109,076 B2
(45) Date of Patent: *Oct. 8, 2024

(54) BIOPSY MARKER WITH ANCHORING CAPABILITIES

(71) Applicant: MED-Genesis, LLC, Clearwater, FL (US)

(72) Inventor: Frederick Ahari, Belleair Beach, FL (US)

(73) Assignee: Med-Genesis, LLC, Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/243,154

(22) Filed: Sep. 7, 2023

(65) Prior Publication Data
US 2023/0414312 A1 Dec. 28, 2023

Related U.S. Application Data

(63) Continuation of application No. 17/076,096, filed on Oct. 21, 2020, now Pat. No. 11,759,285, which is a continuation of application No. 16/877,720, filed on May 19, 2020, now Pat. No. 10,842,591.

(60) Provisional application No. 62/963,707, filed on Jan. 21, 2020.

(51) Int. Cl.
*A61B 90/00* (2016.01)
*A61B 10/02* (2006.01)

(52) U.S. Cl.
CPC ............. *A61B 90/39* (2016.02); *A61B 10/02* (2013.01); *A61B 2010/0208* (2013.01); *A61B 2090/3966* (2016.02); *A61B 2090/3987* (2016.02)

(58) Field of Classification Search
CPC ............. A61B 90/39; A61B 2090/3904–3995
See application file for complete search history.

(56) References Cited

U.S. PATENT DOCUMENTS

| | | | | |
|---|---|---|---|---|
| 5,562,728 | A * | 10/1996 | Lazarus | A61B 17/11 623/1.34 |
| 8,634,899 | B2 * | 1/2014 | Goosen | A61B 90/39 600/431 |
| 2017/0172722 | A1 * | 6/2017 | Dillard | A61B 1/012 |
| 2020/0121414 | A1 * | 4/2020 | Springs | A61B 90/39 |

FOREIGN PATENT DOCUMENTS

CN 110507424 A * 11/2019

* cited by examiner

*Primary Examiner* — Angela M Hoffa
*Assistant Examiner* — Younhee Choi
(74) *Attorney, Agent, or Firm* — Nicholas Pfeifer; Smith & Hopen, P. A.

(57) ABSTRACT

A biopsy marker having a spring-loaded anchor. The biopsy marker includes an insertion orientation and an anchored orientation. In the insertion orientation, the biopsy marker is manipulated under force to reduce the lateral span/cross-sectional area of the marker. In the anchored orientation, the biopsy marker is released and free to actively spring into a configuration in which the lateral span/cross-sectional area is greater than the lateral span/cross-sectional area of the biopsy marker when in the insertion orientation. In an embodiment, the spring-loaded anchor is configured to spring about a predefined rotational axis. An embodiment of the biopsy marker may be comprised of a single wire construction.

19 Claims, 20 Drawing Sheets

Detail C

BIOPSY MARKER WITH ANCHORING CAPABILITIES

CROSS-REFERENCE TO RELATED APPLICATIONS

This nonprovisional application is a continuation of and claims priority to nonprovisional application Ser. No. 17/076,096, entitled "BIOPSY MARKER WITH ANCHORING CAPABILITIES," filed Oct. 21, 2020 by the same inventor(s), which is a continuation of and claims priority to nonprovisional application Ser. No. 16/877,720, entitled "BIOPSY MARKER WITH ANCHORING CAPABILITIES," filed May 19, 2020 by the same inventor(s), which claims priority to provisional application No. 62/963,707, entitled "BIOPSY MARKER WITH ANCHORING CAPABILITIES," filed Jan. 21, 2020 by the same inventor(s).

BACKGROUND OF THE INVENTION

1. Field of the Invention

This invention relates, generally, to biopsy markers. More specifically, it relates to a biopsy marker having spring-loaded anchoring capabilities.

2. Brief Description of the Prior Art

Biopsy markers are used as a means to identify the location of tissue at some later date. Typically, markers are placed in or near the relevant tissue following a biopsy procedure. The marker can then be identified at a later date using imaging equipment, such as an X-Ray machine.

Often, metallic biopsy markers are used alone or in combination with bioabsorbable markers. The metallic markers are not absorbed by the body and can be easily found using imaging equipment. However, metallic markers are susceptible to migration within the tissue. If the marker migrates from its intended position, the marker will no longer identify the biopsy site. The marker effectively becomes useless.

Accordingly, what is needed is a simple, easy to manufacture, and easy to use biopsy marker having an active anchoring means to ensure that the biopsy marker does not migrate from the biopsy site. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a simple, easy to manufacture, and easy to use biopsy marker having an active anchoring means to ensure that the biopsy marker does not migrate from the biopsy site is now met by a new, useful, and nonobvious invention.

An embodiment of the present invention includes a biopsy marker having a bioabsorbable component and a non-bioabsorbable component. The non-bioabsorbable component includes a body section having a predefined non-linear shape. In an embodiment the body section resides at least partially within the bioabsorbable component. The non-absorbable component further includes a spring component residing between an anchoring arm and the body section.

The biopsy marker includes an insertion orientation and an anchoring orientation. The insertion orientation includes the biopsy marker having a cross-sectional area that is less than the cross-sectional area of the biopsy marker when in the anchoring orientation. The insertion orientation further includes the anchoring arm being subject to an external force to overcome a spring force from the spring component. The anchoring orientation includes the anchoring arm being free of the external force and the spring component causes the anchoring arm to spring outward to increase the cross-sectional area of the biopsy marker.

An embodiment includes a non-linear scaffolding section at a distal end of the anchoring arm. In an embodiment the scaffolding includes a j-hook or a barb-like feature to better anchor to a patient's tissue.

In some embodiments, the body section has a coil-shape. In some embodiments, the spring component is a torsion spring. In other embodiments, the spring component is an elbow spring.

In some embodiments, the non-bioabsorbable component is made from a metallic material. In some embodiments, the non-bioabsorbable component is made from a single continuous wire. In some embodiments the bioabsorbable component is comprised of an expandable material that can be dehydrated to reduce its size and hydrated to increase its size.

Some embodiments include the body section residing within the bioabsorbable component when the bioabsorbable component is in a dehydrated state. In addition, a beam extends between the body section and the spring component. The beam has a length greater than a distance between the body section and an outer surface of the bioabsorbable component when in the dehydrated state, such that the spring component resides outside of the bioabsorbable component when in the dehydrated state.

Some embodiments include a second spring component residing between a second anchoring arm and the body section. The insertion orientation further includes the second anchoring arm being subject to an external force to overcome the spring force from the second spring component and the anchoring orientation further includes the second anchoring arm being free of the external force and the second spring component causing the second anchoring arm to spring outward to increase the cross-sectional area of the biopsy marker.

Some embodiments of the present invention include a non-bioabsorbable component of a biopsy marker created from a single wire. In an embodiment, the single wire has a circular cross-sectional shape. Some embodiments include the single wire having a non-circular cross-sectional shape which can impact the direction and amount of spring force. In some embodiments, the non-bioabsorbable component has a coil-shaped body section. A beam extends from the body section to a spring component residing between an anchoring arm and the body section.

The non-bioabsorbable component has an insertion configuration and an anchoring configuration. The non-bioabsorbable component has a smaller cross-section in the insertion configuration than when in the anchoring configuration. In other words, the non-bioabsorbable component, when viewed from an end view (i.e., in line with the longitudinal axis), has a greater outwardly span, relative to the longitudinal axis of the biopsy mark, when in an anchoring orientation than when in an insertion orientation.

The insertion configuration includes the anchoring arm being subject to an external force to overcome a spring force from the spring component and the anchoring configuration includes the anchoring arm being free of the external force and the spring component causes the anchoring arm to spring outward to increase the cross-sectional area/span of the biopsy marker in a lateral/radial direction.

In an embodiment, the non-bioabsorbable component includes a second beam extending from the body section to a second spring component that is connected to a second anchoring arm. The insertion orientation further includes the second anchoring arm being subject to the external force to overcome the spring force from the second spring component. The anchoring orientation further includes the second anchoring arm being free of the external force and the second spring component causes the second anchoring arm to spring outward to increase the cross-sectional area/span of the non-bioabsorbable component.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

As used herein, "substantially perpendicular" will mean that two objects or axis are exactly or almost perpendicular, i.e. at least within five degrees or ten degrees of perpendicular, or more preferably within less than one degree of perpendicular. Similarly, the term "substantially parallel" will mean that two objects or axis are exactly or almost parallel, i.e. are at least within five or ten degrees of parallel and are preferably within less than one degree of parallel.

As used herein, the term "subject," "patient," or "organism" includes humans and animals (e.g., mice, rats, pigs, cats, dogs, and horses).

Figure 1A:
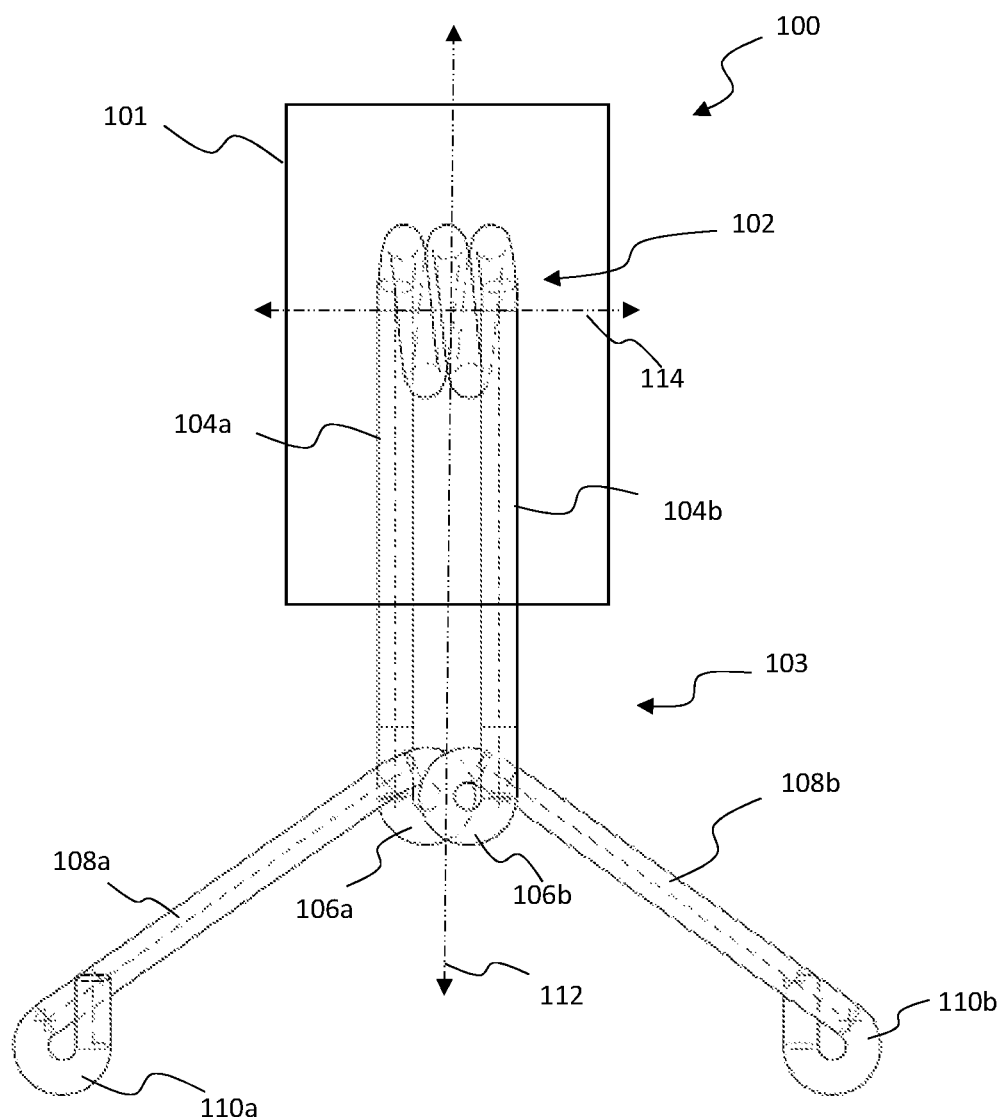
FIG. 1A is a front view of an embodiment of the present invention.
Figure 1B:
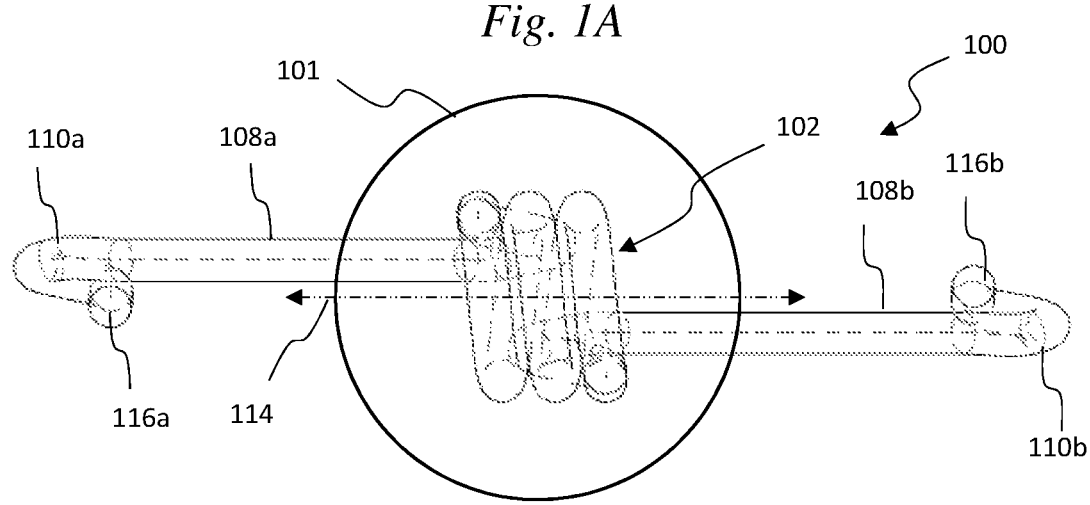
FIG. 1B is a top view of an embodiment of the present invention.
Figure 1C:
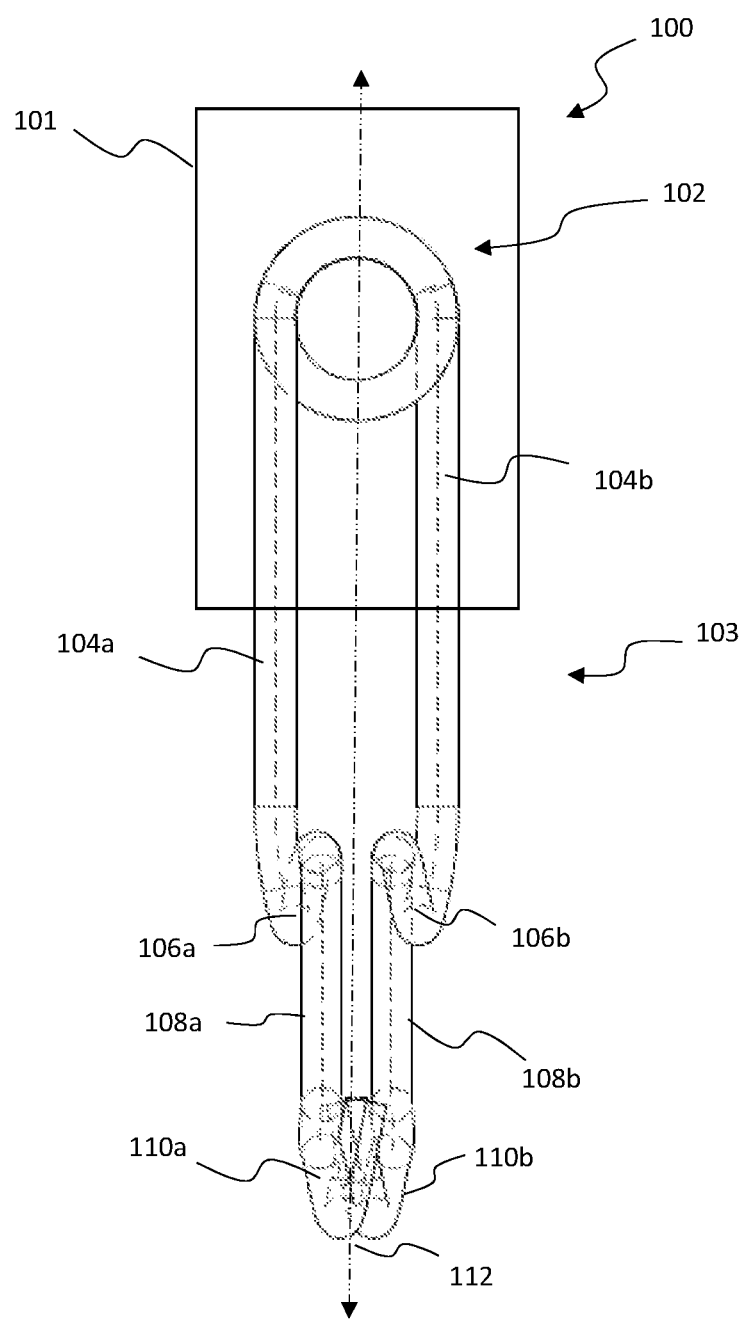
FIG. 1C is a side view of an embodiment of the present invention.

As depicted in FIG. 1, an embodiment of the present invention includes a biopsy marker comprised of bioabsorbable/biodegradable component 101 and non-absorbable component 103. In some embodiments at least a portion of non-absorbable component 103 resides within bioabsorbable component 101. In some embodiments, as will be explained herein, at least body section 102 of non-absorbable component 103 resides within bioabsorbable component 101 and is non-linear and/or multi-dimensional to prevent non-absorbable component 103 from sliding out of bioabsorbable component 101.

In some embodiment, bioabsorbable component 101 is comprised of an expandable material, such as hydrogel, that will expand upon contact with a patient's internal tissue or biological fluids. In some embodiments, bioabsorbable component 101 is comprised of any bioabsorbable material, including but not limited to polyglycolic acid (PGA), polylactic acid (PLA), sugar-based compositions, starch-based compositions, or biological-based composition such as collagen, hydrogel, or any combination of the aforementioned. In some embodiments, bioabsorbable component 101 is a bio-plug designed to close an opening or hole somewhere within a patient's body. The bioabsorbable component may be any size and can be generally any shape. In an embodiment, bioabsorbable component 101 is cylindrical in shape and has a dehydrated cross-sectional size generally equal to the cross-sectional area of an internal lumen of delivery device 202 as shown in FIG. 2.

In some embodiments, at least a portion of non-absorbable component 103 is comprised of one or more metallic materials, including but not limited to nitinol, titanium, and stainless steel. Non-absorbable component 103 will remain within a patient long after bioabsorbable component 101 is absorbed or broken down. Non-absorbable component 103 helps to easily identify biopsy marker 100 using imaging equipment, including but not limited to, X-ray machines, CT scanners, ultrasound machines, or MRI machines. Some embodiments include at least body section 102 of non-absorbable component 103 comprised of a material that is identifiable through at least one imaging machine.

Figure 2A:
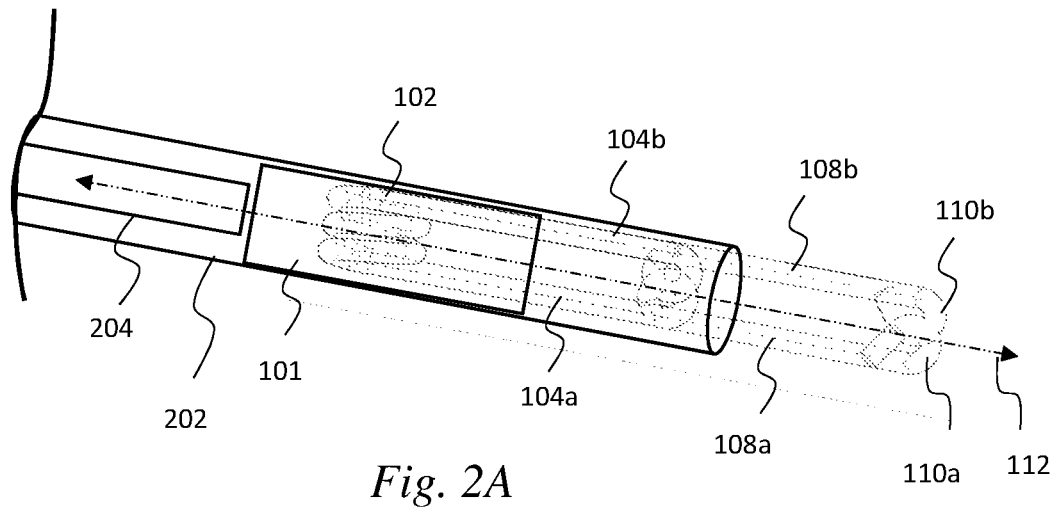
FIG. 2A is an embodiment of the present invention in the insertion configuration within a delivery device.
Figure 2B:
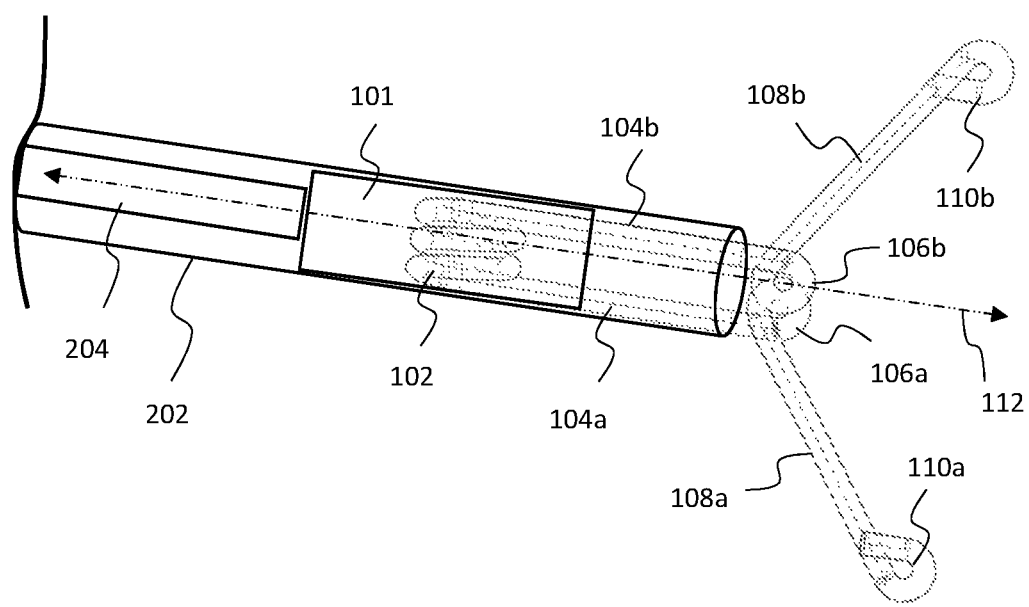
FIG. 2B is an embodiment of the present invention leaving the distal end of a delivery device.
Figure 3A:
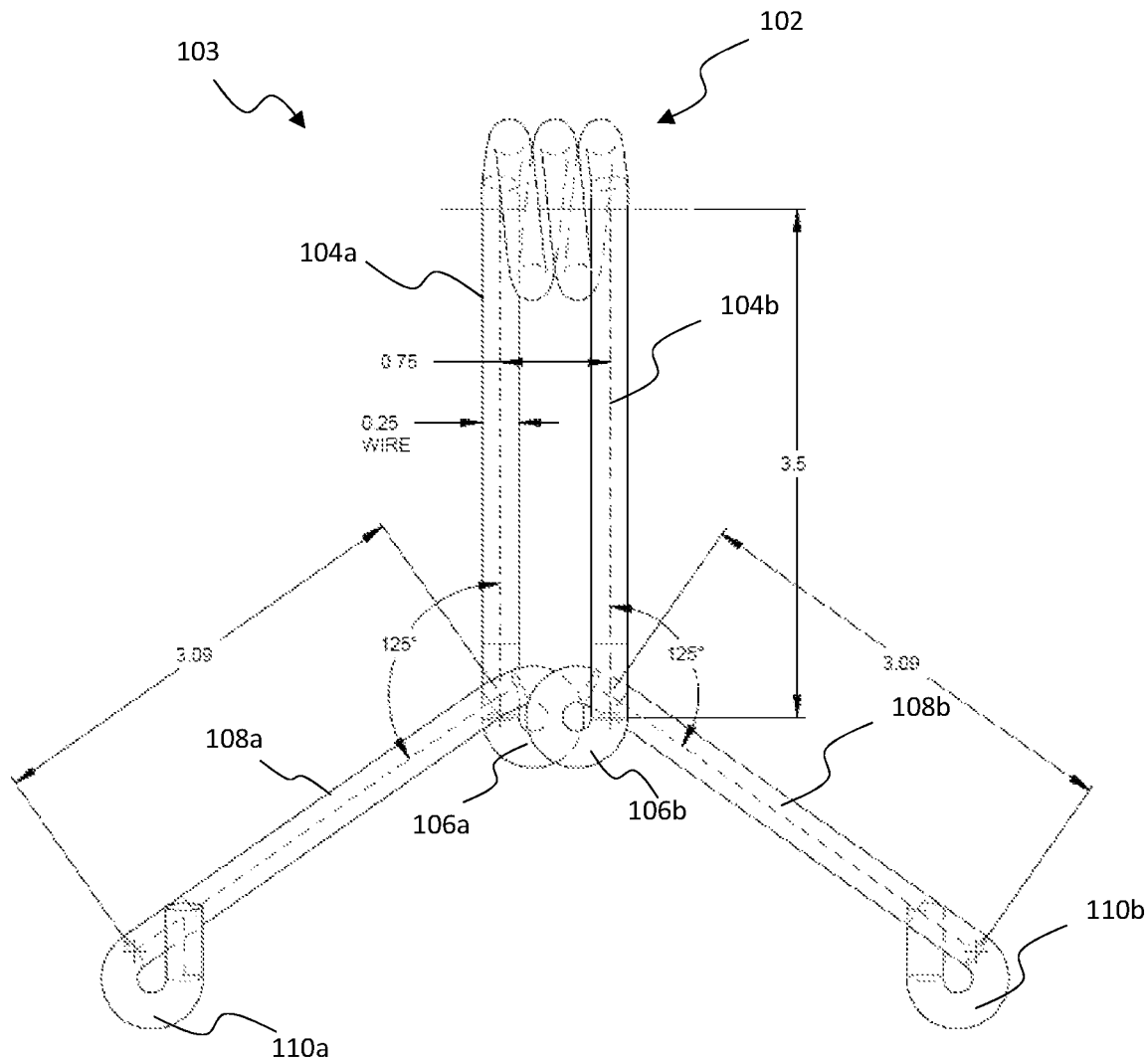
FIG. 3A is a front view of an embodiment of the non-absorbable component.
Figure 3B:
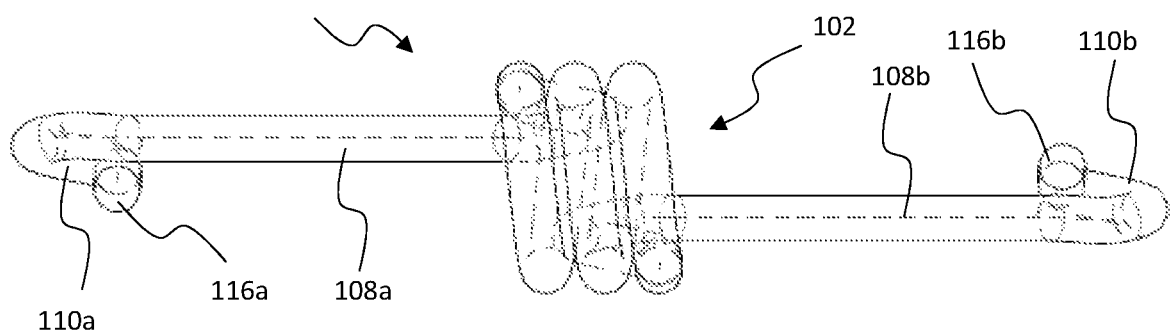
FIG. 3B is a top view of an embodiment of the non-absorbable component.
Figure 3C:
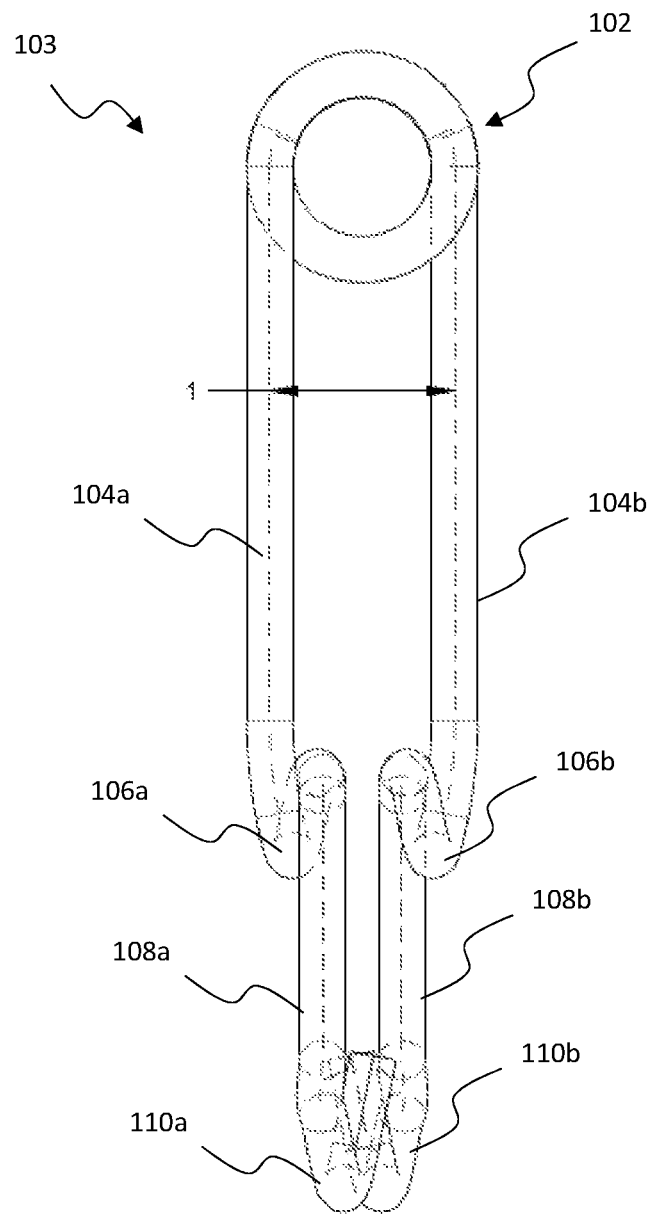
FIG. 3C is a side view of an embodiment of the non-absorbable component.

As depicted in FIGS. 1-3, an embodiment of the present invention includes body section 102 of non-bioabsorbable component 103 residing within bioabsorbable component 101. Body section 102 has a uniquely identifiable shape that (1) provides a means of ensuring that non-bioabsorbable component 103 cannot be easily removed from bioabsorbable component 101 comprised of soft material like hydrogel and (2) helps to easily identify biopsy marker 100 using imaging equipment.

In some embodiments, body section 102 is designed to have a size and shape that cannot pass through the tunnel/canals in bioabsorbable component 101 in which beams 104 reside without rupturing at least one of the canals. In some embodiments, body section 102 is designed to have a size and shape that is larger in cross-section than the canals in bioabsorbable component 101 in which beams 104 reside. Beams 104 provide the structural connection between body section 102 and the anchoring components. If body section 102 is the same size and shape as beam(s) 104, body section 102 could more easily exit bioabsorbable component 101 and potentially cause the two components to become separated from each other prior to the absorption of bioabsorbable component 101. For the same reason, body section 102 as a whole has a size and shape that is larger in cross-section than beam(s) 104. In some embodiments, for the same reason, body section 102 has a shape that is not linear.

The exemplary depicted shape of body section 102 is in the form of a coil. The depicted coil in FIGS. 1-4 includes three interconnected, concentric circles; however, some embodiments have a coil comprised of two interconnected concentric circles (see FIGS. 5-6) to reduce the size of the marker and ultimately the size of the delivery device. An embodiment has body section 102 comprised of a single concentric circle or a body section 102 comprised of a U-shape extending between first and second beams 104a, 104b to further reduce the size of biopsy marker 100 and allow a surgeon to insert the marker using a smaller deliver device. In some embodiments, body section 102 may be any non-linear shape, including but not limited to a horseshoe, a sinusoidal wave, and an M.

As depicted in FIGS. 1-3, body section 102 has central longitudinal axis 114 that is perpendicularly oriented with respect to central longitudinal axis 112 of biopsy marker 100 as a whole. As depicted in FIGS. 4, some embodiments, include coil-shaped body section 102 oriented so that central axis 114 of the coil is coaxial with central longitudinal axis 112 of biopsy marker 100. Some embodiments include central coil axis 114 at an angle between 0 and 90 degrees with respect to longitudinal axis 112 of biopsy marker 100.

In some embodiments, the integrated concentric circles of which the coil is comprised are tightly arranged to minimize the size of body section 102. The spacing between the integrated concentric circles, however, may be adjusted depending on the desired size of body section 102 and the desired amount of resistance to movement within bioabsorbable component 101 as created through variations in the spacing of the integrated concentric circles. The size of the circles of which the coil is comprised can also be adjusted depending on the desired size of body section 102 and the desired amount of resistance to movement within bioabsorbable component 101 as created through variations in the size of the integrated concentric circles.

The size of body section 102 can also be adjusted as needed to fit a specific delivery device 202. Depending on the area of insertion within a patient's body, the cross-sectional area of the internal lumen of delivery device 202 can vary. Ultimately, the cross-sectional size of body section 102 (with respect to longitudinal axis 112 of biopsy marker 100) will be equal to or less than the cross-sectional area of the internal lumen of delivery device 202. In an embodiment, the size of body section 102, extending in a direction parallel to longitudinal axis 112 of biopsy marker 100, will be equal to or less than the length of bioabsorbable component 101 extending in a direction parallel to longitudinal axis 112 of biopsy marker 100. Likewise, an embodiment includes the size of body section 102 extending outwardly in a lateral direction (i.e. perpendicular with respect to longitudinal axis 112) being less than or equal to the size of bioabsorbable component 101 in the same direction.

In some embodiments, body section 102 has a shape that is not a coil shape. In some embodiments, the shape of body section 102 is one that enables the entire non-absorbable component 103 to be comprised of a single continuous wire. In some embodiments, the shape of body section 102 is one that enables body section 102, beams 104, spring 106, and anchoring arms 108 to be comprised of a single wire. In some embodiments, the shape of body section 102 is one that enables body section 102, beams 104, and spring 106 to be comprised of a single wire. In some embodiments, the shape of body section 102 is one that enables body section 102 and beams 104 to be comprised of a single wire. In some embodiments, the shape of body section 102 is one that can be comprised of a single wire.

Some embodiments of the present invention include multiple biopsy markers with each having a visibly distinct variation in the shape of body sections 102. The variation in shapes of body sections 102 between different biopsy markers allows multiple biopsy markers to be inserted into a patient with each remaining visibly distinct when viewed through imaging equipment. For example, the coil shape, number of coils, orientation of the coil, size of the coil, size of the concentric circles of the coil, or spacing between circles within a coil can be adjusted to ensure that various biopsy markers can be differentiated from each other using imaging equipment. Likewise, different shapes of body section 102 between various biopsy markers can be used. For example, different biopsy markers may have a body section 102 shaped as a coil, a horseshoe, a sinusoidal wave, an M, etc. Preferably the shapes are those which can be created by manipulating or bending a single wire.

Biopsy marker 100 of the present invention further includes at least one beam 104 extending away from body section 102 towards spring 106. The one or more beams 104 provide the mechanical interconnection between body section 102 and springs 106. In some embodiments, beam(s) 104 extend in a direction generally parallel to longitudinal axis 112 of biopsy marker 100. Extending in this direction helps to limit the cross-sectional area of biopsy marker 100. Some embodiments include beams 104 extending from body section 102 in a direction that is not generally parallel with longitudinal axis 112.

As depicted in FIGS. 1-4, some embodiments include two beams 104a, 104b. In FIGS. 1-3, both beams 104a, 104b extend in generally the same direction. Alternatively, FIG. 4 illustrate how some embodiments include beams 104a, 104b extending in generally opposite directions. Some embodiments may have more than two beams 104 and thus more than 2 springs 106, anchoring arms 108, and scaffoldings 110.

Figure 4A:
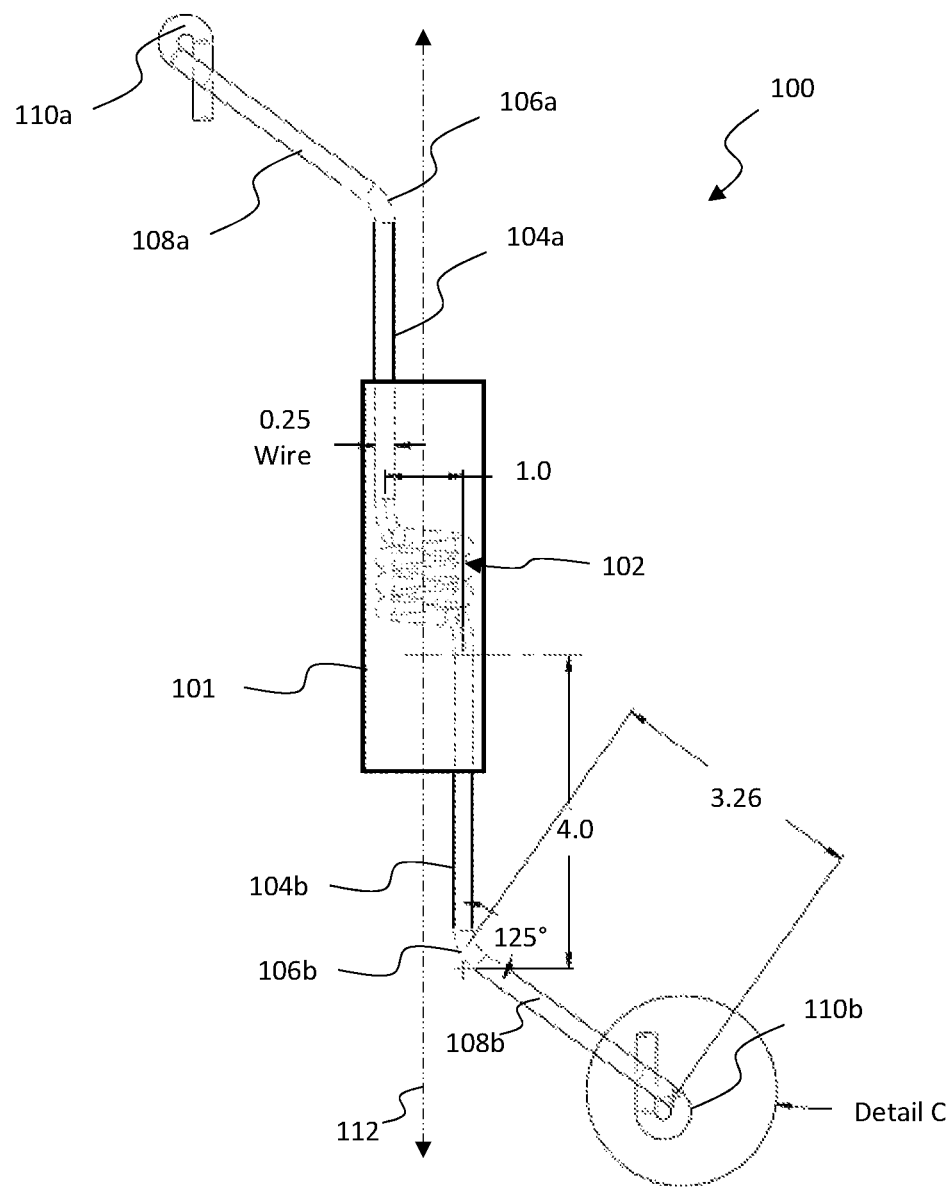
FIG. 4A is a front view of an embodiment of the present invention.
Figure 4B:
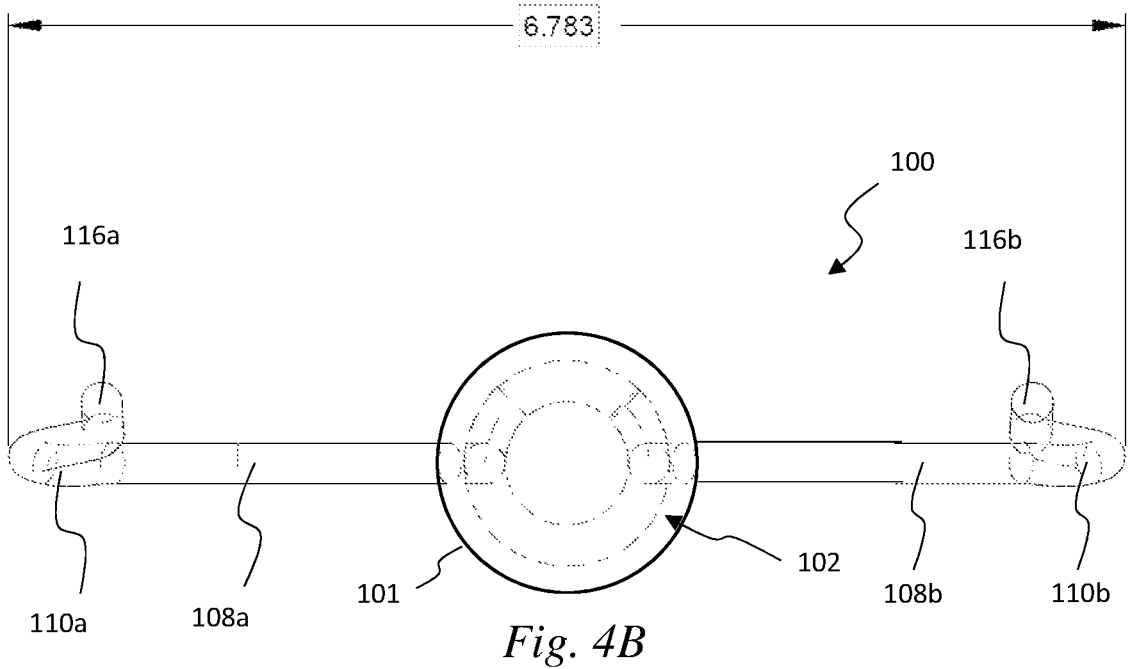
FIG. 4B is a top view of an embodiment of the present invention.
Figure 4C:
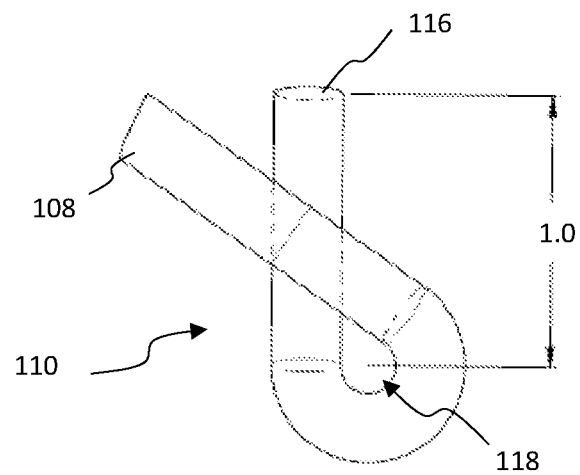
FIG. 4C is a close-up view of detail C from FIG. 4A.
Figure 4D:
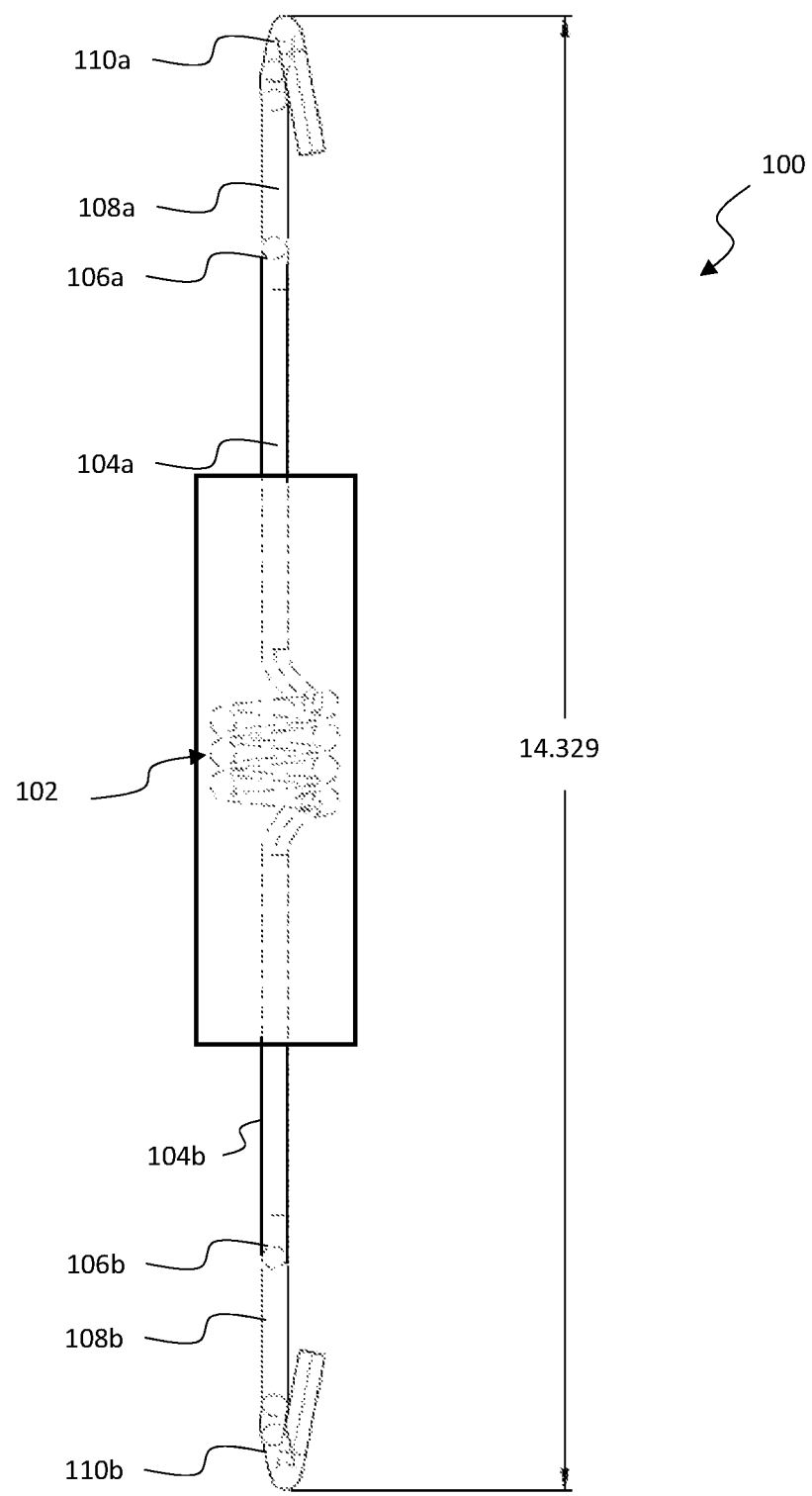
FIG. 4D is a side view of an embodiment of the present invention.
Figure 5:
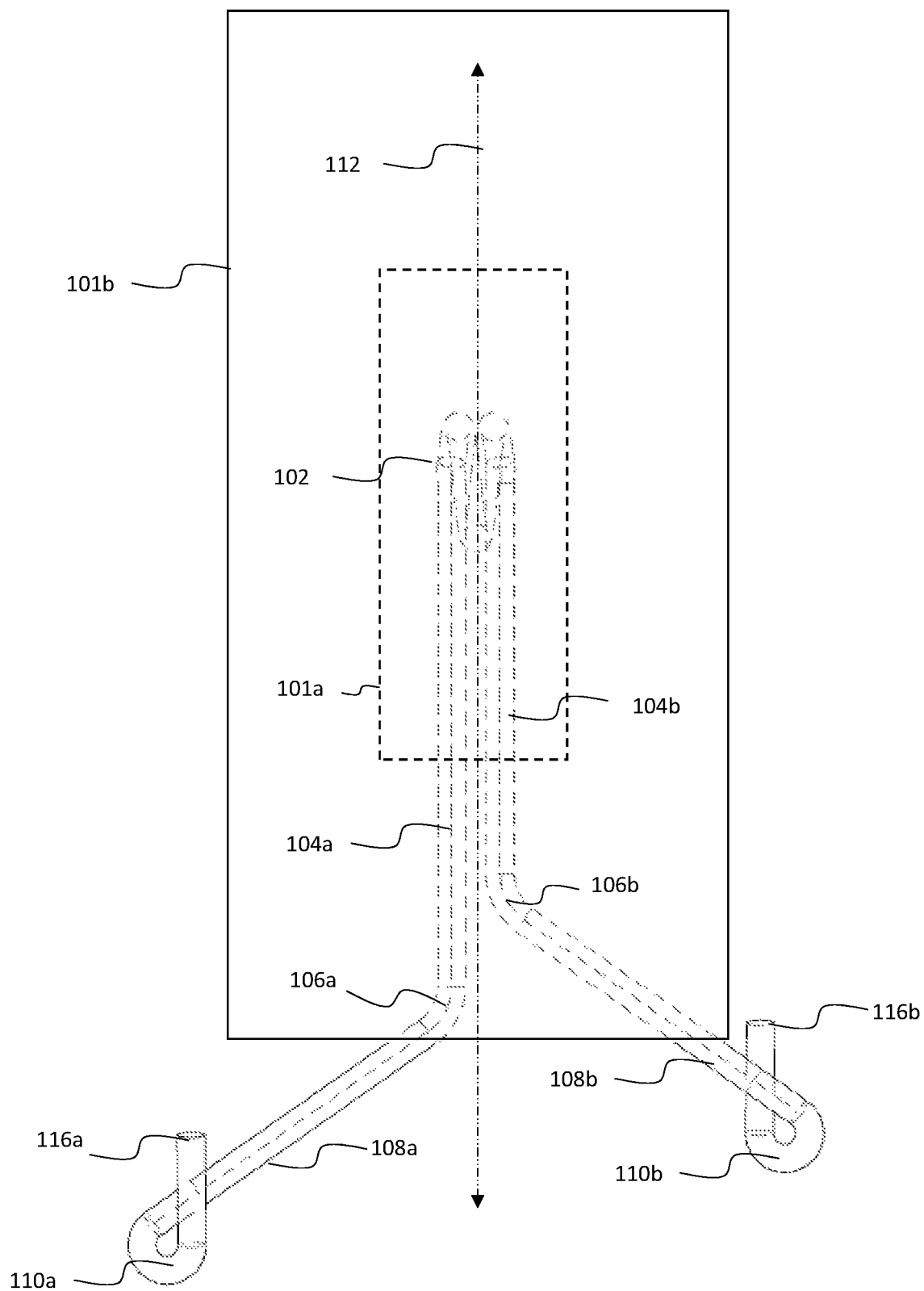
FIG. 5 is a front view of an embodiment of the present invention.
Figure 6A:
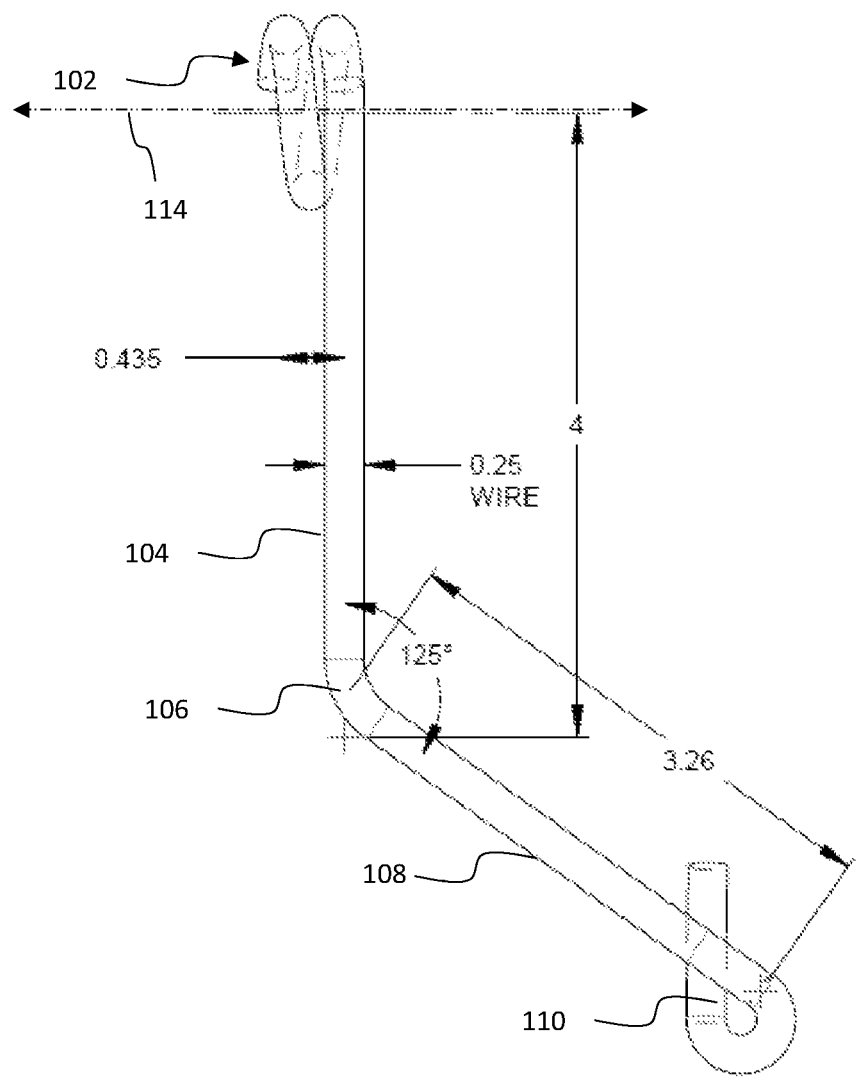
FIG. 6A is a front view of an embodiment of the non-absorbable component.
Figure 6B:
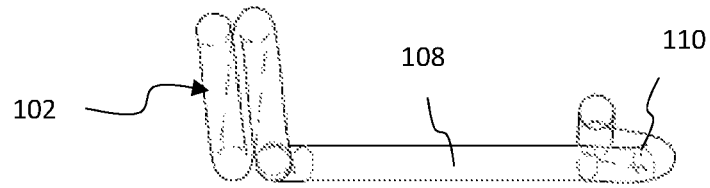
FIG. 6B is a top view of an embodiment of the non-absorbable component.
Figure 6C:
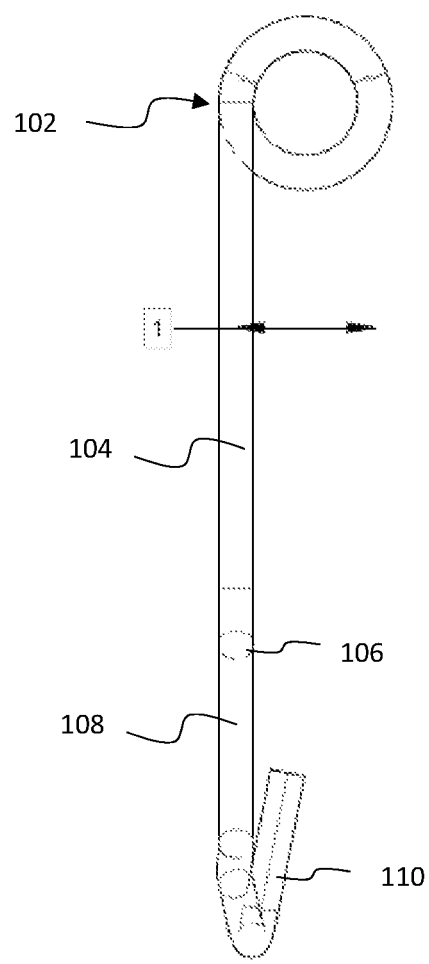
FIG. 6C is a side view of an embodiment of the non-absorbable component.
Figure 6D:
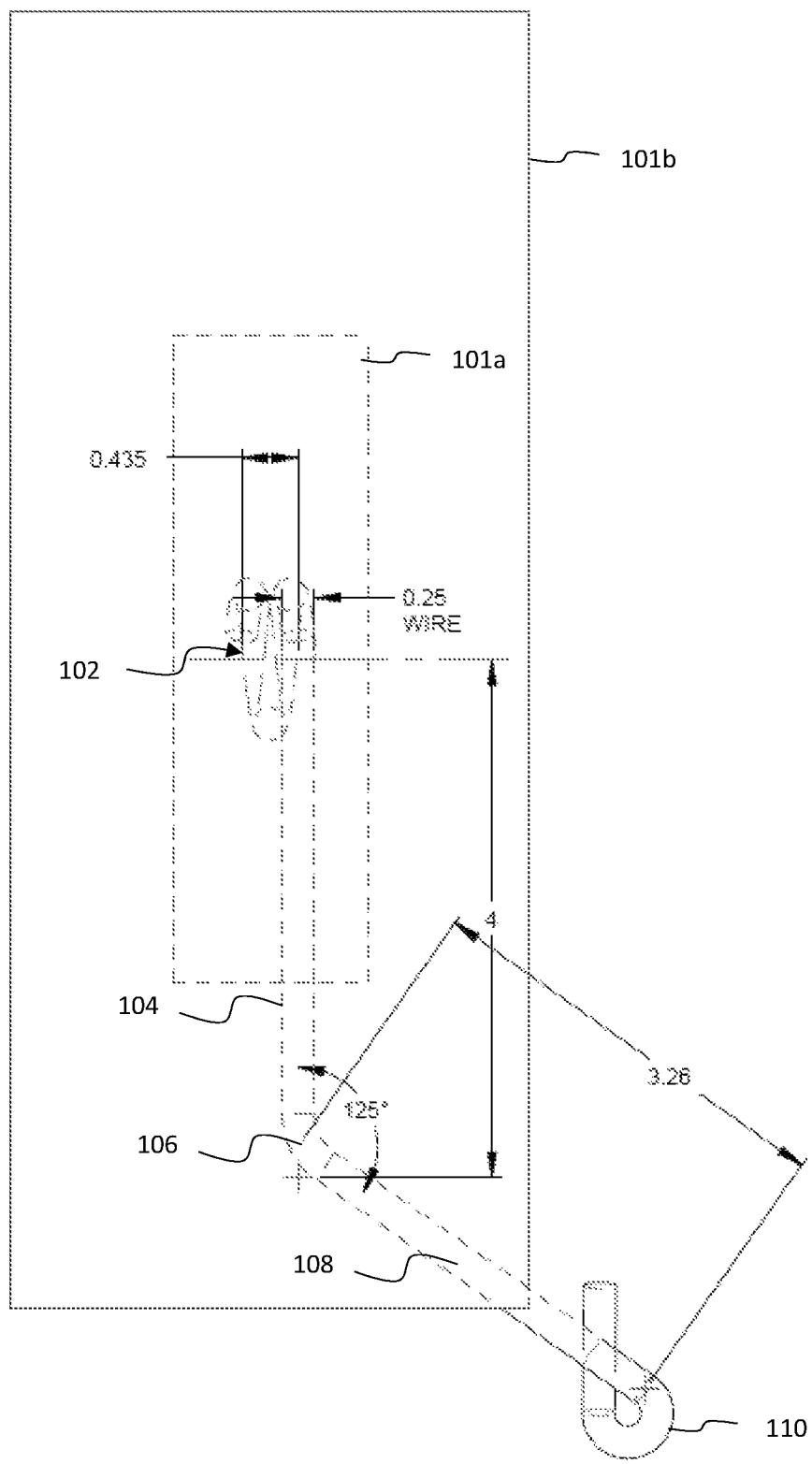
FIG. 6D is a front view of FIG. 6A with the bioabsorbable component shown in both a dehydrated and hydrated stage.
Figure 6E:
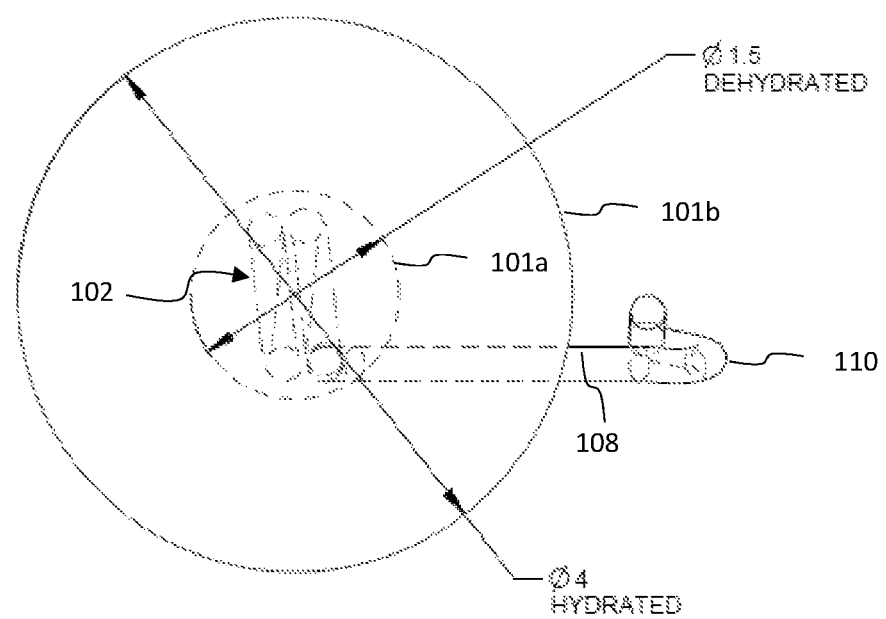
FIG. 6E is a top view of FIG. 6B with the bioabsorbable component shown in both a dehydrated and hydrated stage.
Figure 6F:
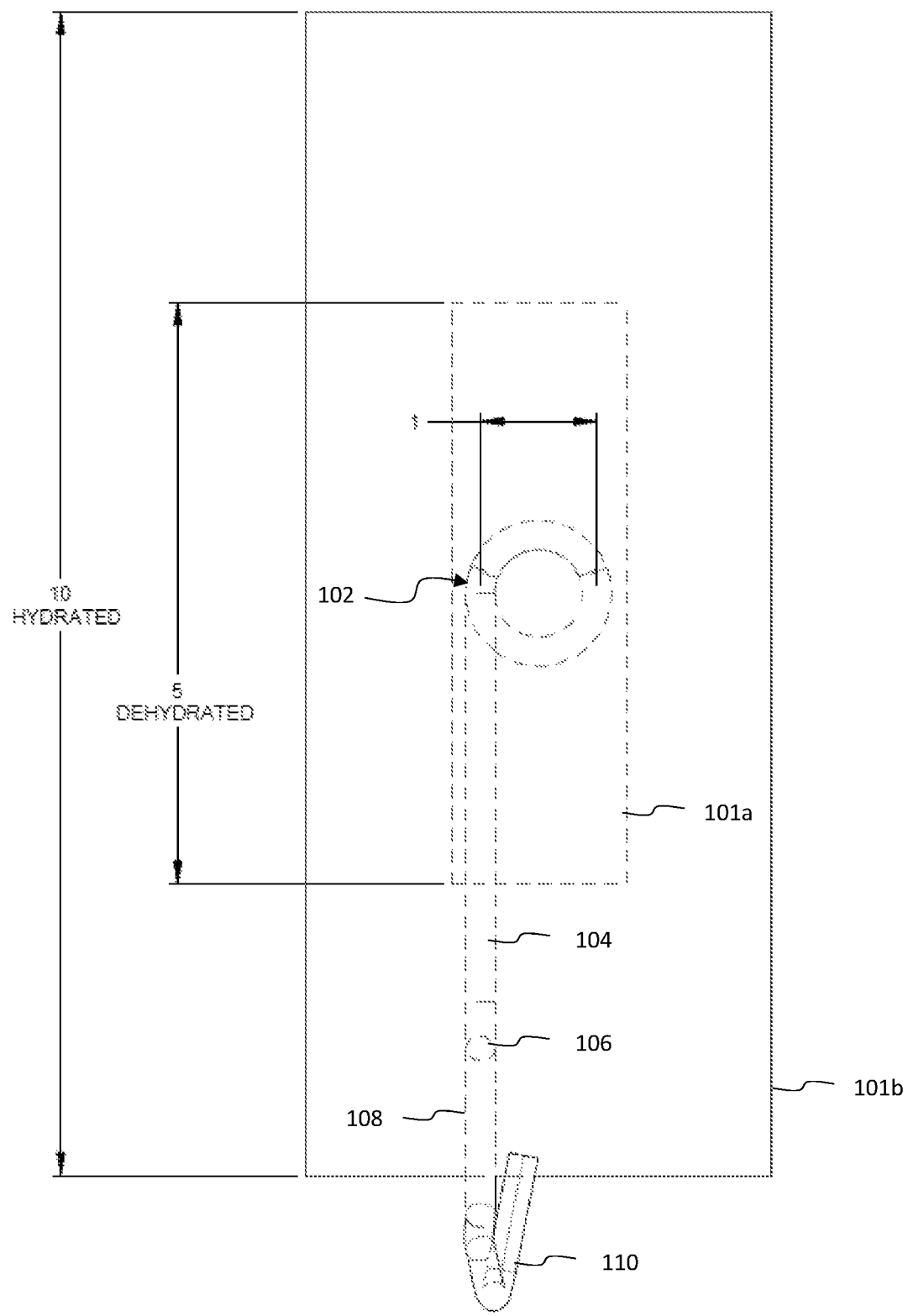
FIG. 6F is a side view of FIG. 6C with the bioabsorbable component shown in both a dehydrated and hydrated stage.

In some embodiments, beams 104a, 104b may be the same length as shown in FIG. 4 or may have different lengths as depicted in FIG. 5. With different length beams 104a, 104b, springs 106a, 106b reside at different locations along the length of biopsy marker 100 and thus occupy less space in a lateral/radial direction (i.e., perpendicular direction with respect to longitudinal axis 112) than if springs 106a, 106b occupied the same location along the longitudinal extent of biopsy marker 100. Ultimately, this reduction in space allows for the use of a smaller diameter delivery device 202.

Some embodiments, such as the ones depicted in FIGS. 6 and 7, include a single beam 104 extending between body section 102 and spring 106. In some embodiments as depicted in FIGS. 6, beams 104 extend in a direction generally perpendicular to central longitudinal axis 114 of body section 102. As depicted in FIGS. 7, some embodiments include beams 104 extending in a direction generally parallel to central longitudinal axis 114 of body section 102.

In some embodiments, as depicted in FIGS. 6 and 7, spring(s) 106 resides outside of bioabsorbable component 101 when bioabsorbable component 101 is in a dehydrated state prior to and initially during the process of inserting biopsy marker 100 into a patient. Because spring(s) 106 resides outside of bioabsorbable component 101a when in a dehydrated state, beam(s) 104 have a length greater than the distance between body section 102 and an outer surface, such as a longitudinal end, of bioabsorbable component 101a when in the dehydrated state. In some embodiments, beams 104 have a length sufficient to ensure that scaffoldings 110 resides longitudinally beyond the longitudinal end of bioabsorbable component 101 when in a hydrated state 101b. In some embodiments, as depicted in FIG. 8, beams 104 have a length greater than the distance between body section 102 and a longitudinal end of bioabsorbable component 101 when in a hydrated state as identified by reference numeral 101b.

The present invention further includes non-absorbable component 103 having at least one spring-loaded anchor comprised of spring component 106 (also referred to as "spring 106"), anchoring arm 108 and scaffolding 110. Springs 106 are located at the end of beam 104 opposite of the end attached to or integrated with body section 102 of biopsy marker 100. Springs 106 allow their respective anchoring arms 108 to actively spring into an anchoring position to secure biopsy marker 100 at the biopsy site.

At least spring 106 is comprised of a resilient material, such as nitinol, titanium, or stainless steel, so that biopsy marker 100 can be forced into an insertion configuration and can then rebound into an anchoring configuration when disposed within a patient's body. In some embodiments, spring component 106, anchoring arm 108 and scaffolding 110 are comprised of one or more resilient materials. In other embodiments, the entire non-absorbable component 103 is comprised of resilient material(s).

As provided in FIGS. 1-3, springs 106 are depicted as torsion springs. The first end of each torsion spring is integrated with beam 104 and the second end of each torsion spring is integrated with anchoring arm 108. An embodiment of the spring component, however, may include active springs of other designs known to a person of ordinary skill in the art, including but not limited to elbow springs, loop springs, leaf springs, helical springs, compression springs, plate springs, etc. Spring 106 includes a position of repose in which the angle between the respective beam 104 and the respective anchoring arm 108 does not equal 180 degrees.

As depicted in FIGS. 4-9, spring 106 is an elbow spring. The elbow spring is easier to manufacture when non-bioabsorbable component 103 is comprised of a single wire. Elbow spring 106 has a position of repose in which the angle between the respective beam 104 and the respective anchoring arm 108 does not equal 180 degrees. The elbow spring, however, may be bent out of its position of repose when subject to external forces.

In an embodiment, spring 106 is designed so that the angle between beam 104 and anchoring arm 108 is about 125 degrees when spring 106 is in a position of repose. Some embodiments include spring 106 having a position of repose in which the angle between beam 104 and anchoring arm 108 is between 90 and 180 degrees. Some embodiments include spring 106 having a position of repose in which the angle between beam 104 and anchoring arm 108 is between 100 and 160 degrees. Some embodiments include spring 106 having a position of repose in which the angle beam 104 and anchoring arm 108 is sufficient to ensure that scaffolding 110 is outside of hydrogel in both the hydrated and dehydrated states.

In an embodiment, spring component 106 includes a structure that defines a hinge/rotational axis disposed between its respective beam 104 and anchoring arm 108. In other words, the spring capability is associated with structural components and features beyond simply bending a resilient member.

As previously explained, spring 106 allows non-bioabsorbable component 103 to be manipulated into an insertion configuration. In the insertion configuration, anchoring arm 108 and in turn scaffolding 110 are manipulated under a force greater than the spring force of spring 106. Anchoring arm 108 and in turn scaffolding 110 are forced towards central longitudinal axis 112 to reduce the cross-sectional area of biopsy marker 100 so that biopsy marker 100 fits within an internal lumen of delivery device 202 as depicted in FIG. 2A. Delivery device 202 can be any needle, catheter, or any other bio-insertable tubular structure that can be inserted into a patient to deliver biopsy marker 100 to a biopsy site. In some embodiments, spring 106 is adapted to permit anchoring arm 108 and scaffolding 110 to be forced towards central longitudinal axis 112 until non-absorbable component 103 has a cross-sectional area that is equal to or smaller than the cross-sectional area of bioabsorbable component 101.

When biopsy marker 100 is inserted into a patient, biopsy marker 100 is forced out of delivery device 202, using e.g. plunger device 204, and anchoring arm 108 and in turn scaffolding 110 spring into the anchoring configuration under the spring force from spring 106 when they exit the internal lumen of delivery device 202 as depicted in FIG. 2B. In the anchoring configuration, the lateral/radial span, i.e. cross-sectional area, of biopsy marker 100 is greater than the cross-sectional area when biopsy marker 100 is in the insertion configuration. Typically, the anchoring arms 108 will spring outwardly away from central longitudinal axis 112. Depending on the resiliency of the material of the non-absorbable component 103 or the spring force of spring 106 and/or the density of the surrounding tissue into which biopsy marker 100 is deposited, the one or more anchoring arms 108 will return to their respective positions of repose or spring outwardly until the spring force of spring 106 equals the force of the tissue on the anchor assembly.

In some embodiments, springs 106 reside outside of bioabsorbable component 101 when bioabsorbable component 101 is in a dehydrated state. In some embodiment, springs 106 reside outside of bioabsorbable component 101 when bioabsorbable component 101 is in a hydrated state. In some embodiment, springs 106 reside outside of bioabsorbable component 101 when bioabsorbable component 101 is in a dehydrated state, but not when bioabsorbable component 101 is in a hydrated state.

Anchoring arm(s) 108 extend further beyond spring(s) 106 in a direction away from body section 102. Anchoring arms 108 are designed to engage tissue within a patient and project scaffolding(s) 110 further from body section 102 to engage tissue within a patient. Depending on the embodiment, biopsy marker 100 may have one or more anchoring arms 108. Typically, biopsy marker 100 will have one anchoring arm 108 for every spring 106.

In some embodiments, anchoring arms 108 has a length greater than or equal to the distance (in the same direction of anchoring arm 108 when in a position of repose) between spring 106 and an edge of bioabsorbable component 101 when in a hydrated state. As a result, scaffolding 110 engages a patient's tissue rather than bioabsorbable component 101. In some embodiments having more than one anchoring arm 108, one anchoring arm has a length greater than the other so that scaffoldings 110 are longitudinally spaced from each other and can thus occupy less lateral/radial space when in the insertion orientation.

In some embodiments, anchoring arms 108 are a continuation of the single wire of which other portions of nonabsorbable component 103 is comprised. In some embodiments, anchoring arms 108 have the same cross-sectional size of portions of nonabsorbable component 103. In some embodiments, anchoring arms 108 have a larger cross-sectional size than other portions of nonabsorbable component 103 to help anchoring arms 108 engage the patient's tissue.

In some embodiments, anchoring arms 108 have a circular-shaped cross-section. In some embodiments, anchoring arms 108 have a cross-sectional shape that is not circular to increase friction with a patient's tissue and ultimately help anchoring arms 108 engage the patient's tissue. In some embodiments, anchoring arms 108 have an outer surface with friction increasing elements or friction increasing materials to help anchoring arms 108 engage the patient's tissue.

The present invention further includes one or more scaffoldings 110 at a distal end of anchoring arms 108. Some embodiments include scaffoldings 110 attached to or integrated with each anchoring arm 108. Scaffoldings 110 provides another anchoring means and structural support for tissue growth post deployment. The tissue growth on and around scaffoldings 110 helps to prevent biopsy marker 100 from migrating away from the biopsy site.

In an embodiment, each scaffolding 110 has a non-linear shape. In some embodiments, scaffoldings 110 have a loop shape, which is best seen in FIG. 4C. As depicted therein, distal most end 116 of scaffolding 110 extends beyond anchoring arm 108 in forming the loop shape. The extension of distal end 116 beyond anchoring arm 108 or the other portions of scaffolding 110 ensure that distal end 116 is more capable of hooking into the patient's tissue. In addition, the loop shape is designed to leave hole 118 through which tissue can grow providing better purchase on scaffolding 110. Other embodiments may not include distal most end 116 extending beyond anchoring arm 108 and/or may not include hole 118.

In some embodiments as depicted best in FIG. 1B, distal ends 116 of each scaffolding 110 are looped inwards towards central longitudinal axes 112 and 114. In some embodiments as depicted best in FIG. 4B, distal ends 116 of each scaffolding 110 are looped outwards away from central longitudinal axes 112 and 114 in the same direction. In some embodiments, distal ends 116 of each scaffolding 110 are looped outwards away from central longitudinal axes 112 and 114 in opposite directions. In some embodiments as depicted best in FIG. 5, distal ends 116 of each scaffolding 110 are looped outwards away from central longitudinal axes 112 and 114 and away from each other. The orientation of the loops and the direction of distal ends 116 are optimized to reduce the lateral/radial space that scaffolding 110 occupy when in the insertion orientation. As a result, the internal lumen and thus delivery device 202 as a whole can be reduced in cross-section to limit the size of the opening in a patient's body.

In some embodiments, includes scaffolding 110 having a barb-like shape or a J-hook shape at distal end 116. The barb-like shape or a J-hook shape of distal end 116 is oriented in a way to prevent anchoring arm 108 from moving back towards an insertion orientation or towards the insertion site. In some embodiments, scaffolding 110 is any non-linear shape to prevent anchoring arm 108 from moving back towards an insertion orientation or towards the insertion site.

In some embodiments, scaffoldings 110 are a continuation of the single wire of which other portions of nonabsorbable component 103 are comprised. In some embodiments, scaffoldings 110 have the same cross-sectional size of portions of nonabsorbable component 103. In some embodiments, scaffoldings 110 have a larger cross-sectional size than other portions of nonabsorbable component 103 to help scaffoldings 110 engage the patient's tissue. In some embodiments, scaffoldings 110 have a circular-shaped cross-section. In some embodiments, scaffoldings 110 have a cross-sectional shape that is not circular to increase friction with a patient's tissue and ultimately help scaffoldings 110 engage the patient's tissue. In some embodiments, scaffoldings 110 have an outer surface with friction increasing elements or friction increasing materials to help scaffoldings 110 engage the patient's tissue.

During operation, biopsy marker 100 of the present invention has a size and shape that can be inserted into a patient using a bio-compatible delivery device 202. Biopsy marker 100 is forced into the insertion orientation shown in FIG. 2A. In the insertion orientation, anchoring arms 108 are forced into a position in which the cross-sectional area of biopsy marker 100 is reduced to fit within the internal lumen of delivery device 202. This position includes anchoring arms 108 folded up and towards body section 102 in some embodiments (not shown) or down and away from the body section 102 as shown in FIG. 2A to bring the angle between beams 104 and anchoring arms 108 to or near 180 degrees. Biopsy marker 100 is then forced into the inner lumen of delivery device 202 and the inner lumen holds biopsy marker 100 in the insertion orientation.

Delivery device 202 is either already in position or is inserted into position at the biopsy site. The entry point into the biopsy site is thus generally the size of the cross-sectional area of the delivery device 202. Biopsy marker 100 can then be forced out of a distal end of the delivery device 202 and upon exiting delivery device 202, anchoring arms 108 actively spring outward into a position of repose (or as close to a position of repose as a patient's tissue allows) and biopsy marker 100 anchors itself into the tissue at the biopsy site. In the anchoring orientation, the span/cross-sectional area of biopsy marker 100 is greater than the cross-sectional area of delivery device 202. As a result, biopsy marker cannot exit the entry point into the biopsy site when biopsy marker 100 is in the anchoring orientation. The active spring action into the anchoring orientation ensures that biopsy marker 100 will remain at its insertion point.

In some embodiments, as best depicted in FIGS. 5, 6D-6F, and 7D-7F, bioabsorbable component 101 is an expandable material such as hydrogel. Bioabsorbable component 101 plays at least two roles. One role is to aid in imaging. By disposing biopsy marker 100 in hydrogel or another absorbable substance, biopsy marker 100 is more easily visible during ultrasound scans after being embedded within a patient. Ultrasound imaging shows air and water really well, so bioabsorbable component 101 shows up as a black area in an ultrasound image. Because at least body section 102 is disposed within the hydrogel of bioabsorbable component 101, the hydrogel surrounds body section 102 during a curing process to bind the components together. The metallic structure of non-bioabsorbable component 103 residing within bioabsorbable component 101 shows up as air, in white, and provides an easily identifiable contrast to locate biopsy marker 100. Imaging equipment is therefore able to easily identify biopsy marker 100.

The other role of bioabsorbable component 101 is tied to its expandable nature. Prior to and during insertion, bioabsorbable component is in a dehydrated state identifiable by reference numeral 101a, as shown in FIGS. 6D-6F, and 7D-7F. The size/surface area of bioabsorbable component 101 is smaller in the dehydrated stage as compared with the hydrated stage. Using an expandable bioabsorbable component 101 allows for the biopsy marker to be reduced in size for insertion into a patient and expand to fill holes or voids in patient tissue when deployed.

Figure 7A:
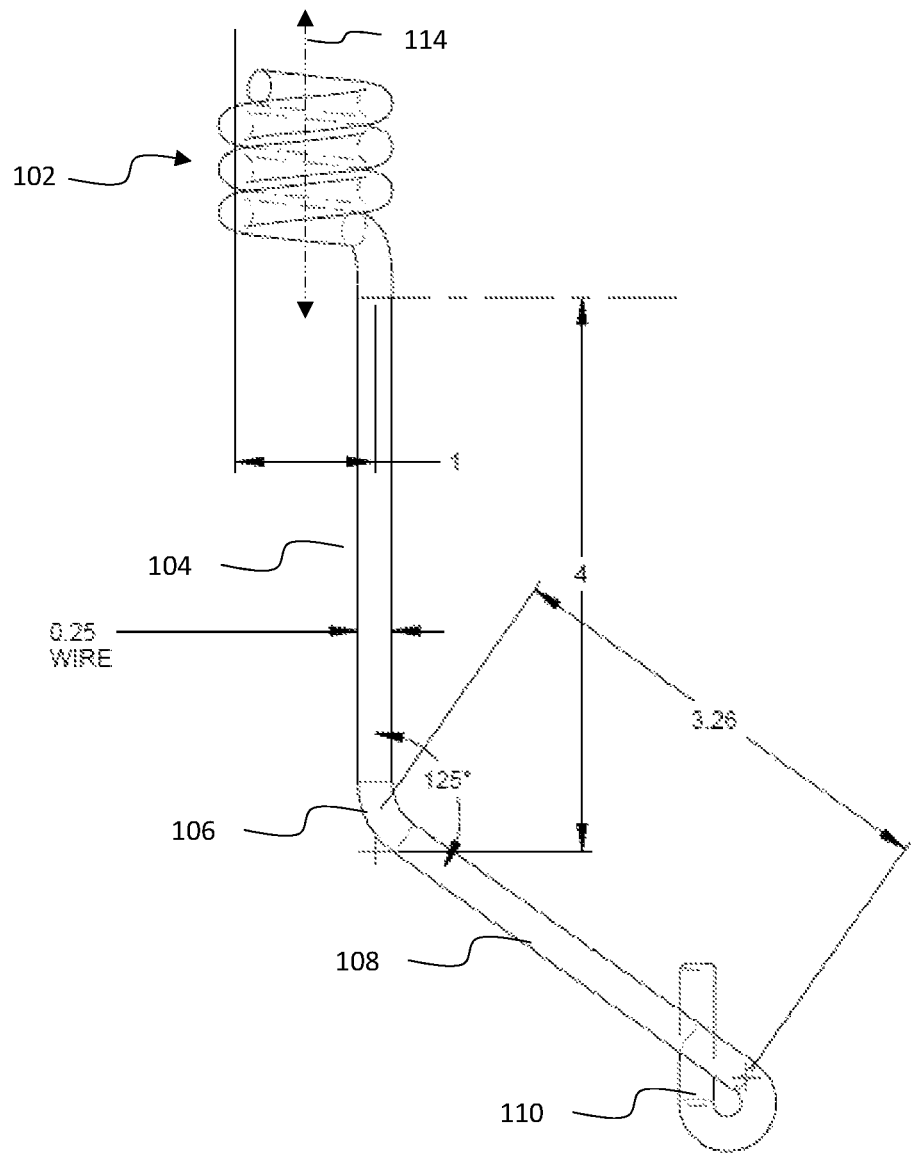
FIG. 7A is a front view of an embodiment of the non-absorbable component.
Figure 7B:
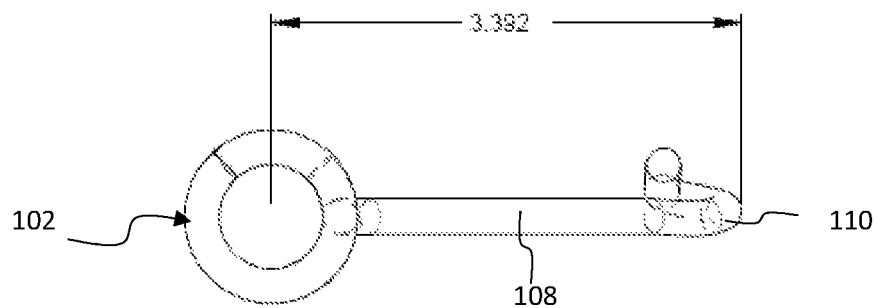
FIG. 7B is a top view of an embodiment of the non-absorbable component.
Figure 7C:
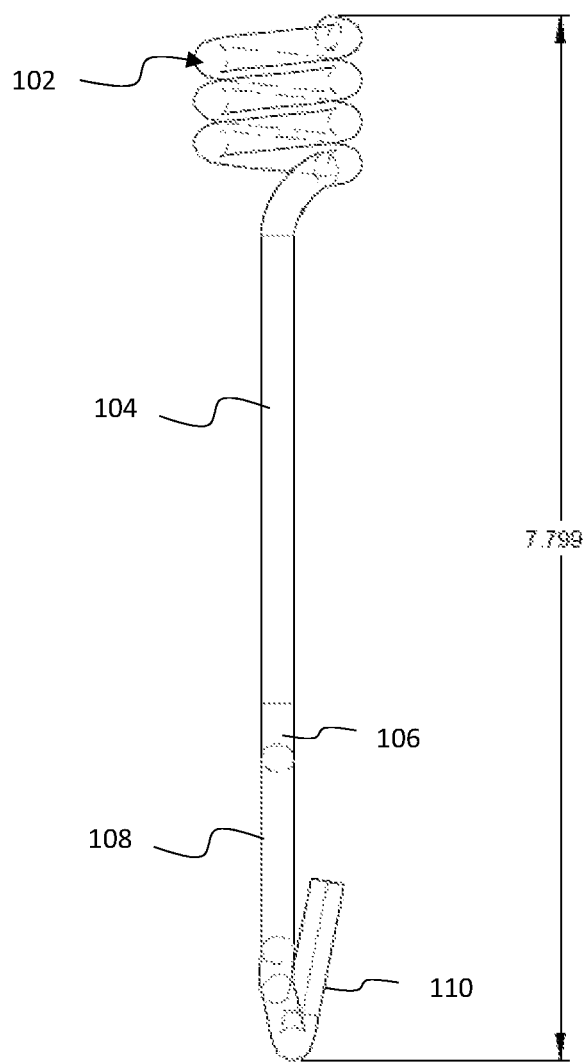
FIG. 7C is a side view of an embodiment of the non-absorbable component.
Figure 7D:
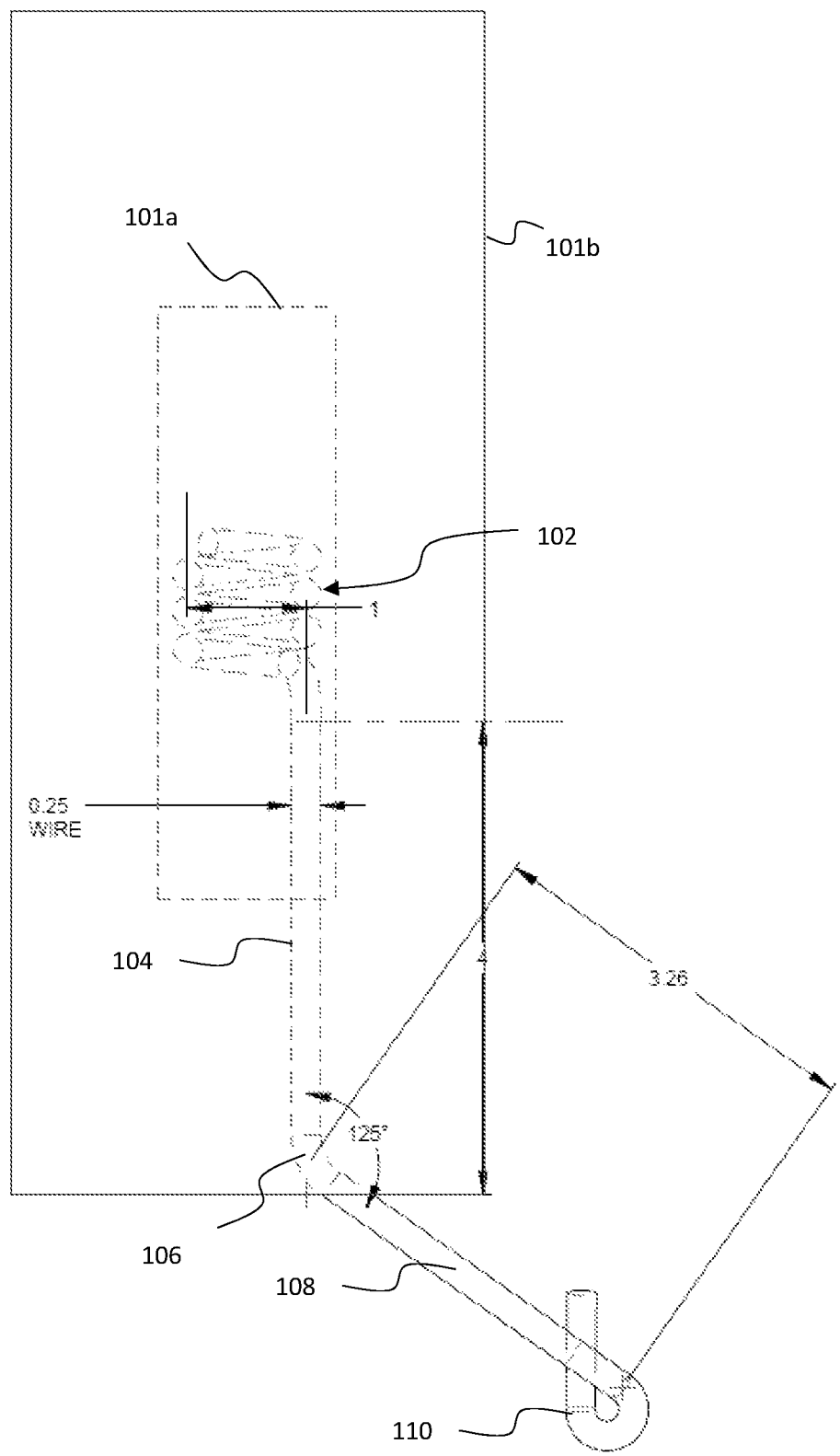
FIG. 7D is a front view of FIG. 7A with the bioabsorbable component shown in both a dehydrated and hydrated stage.
Figure 7E:
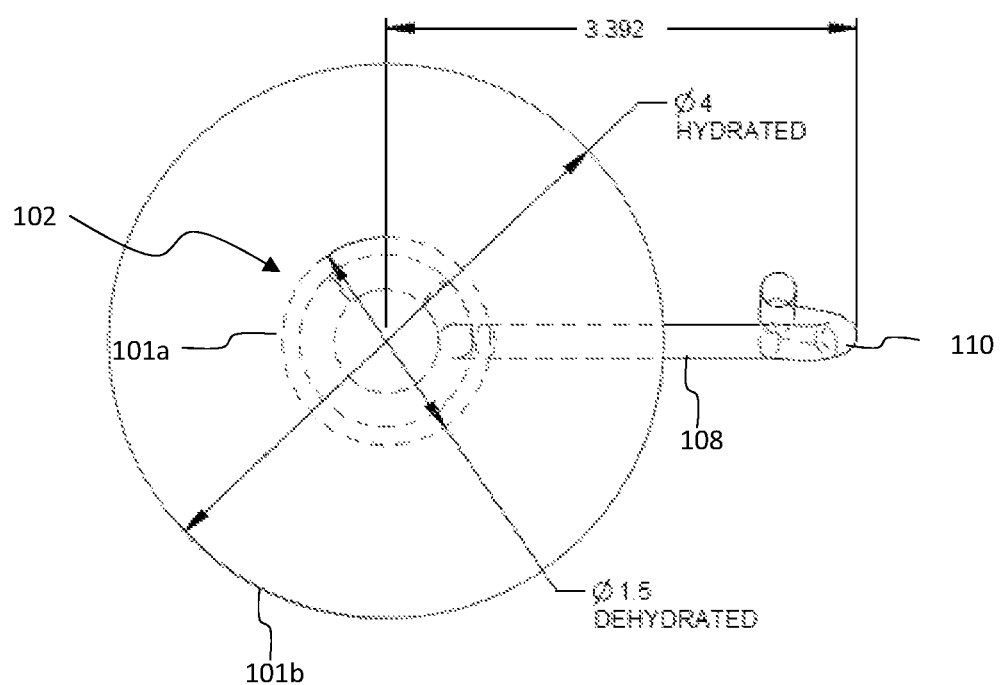
FIG. 7E is a top view of FIG. 7B with the bioabsorbable component shown in both a dehydrated and hydrated stage.
Figure 7F:
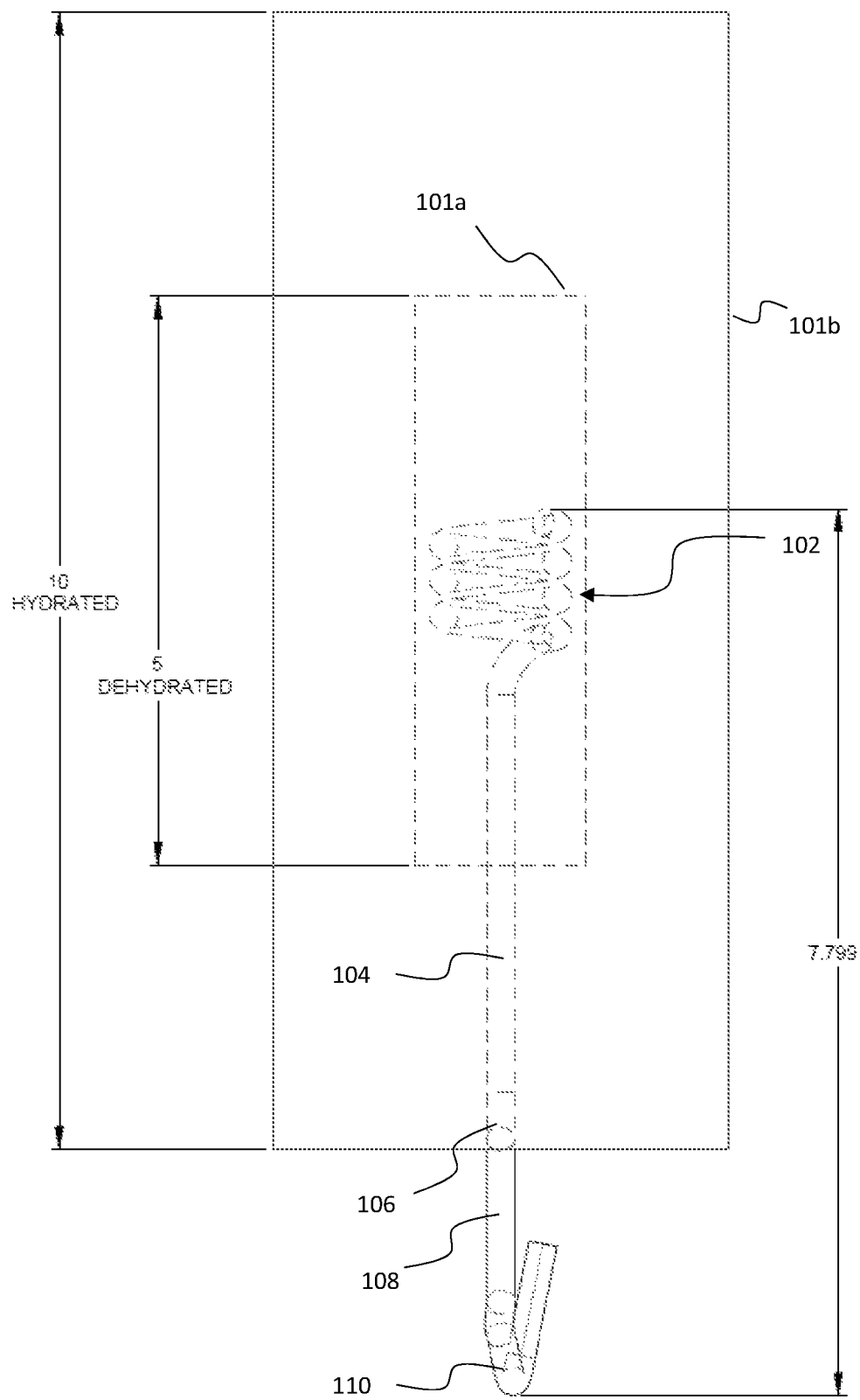
FIG. 7F is a side view of FIG. 7C with the bioabsorbable component shown in both a dehydrated and hydrated stage.
Figure 8:
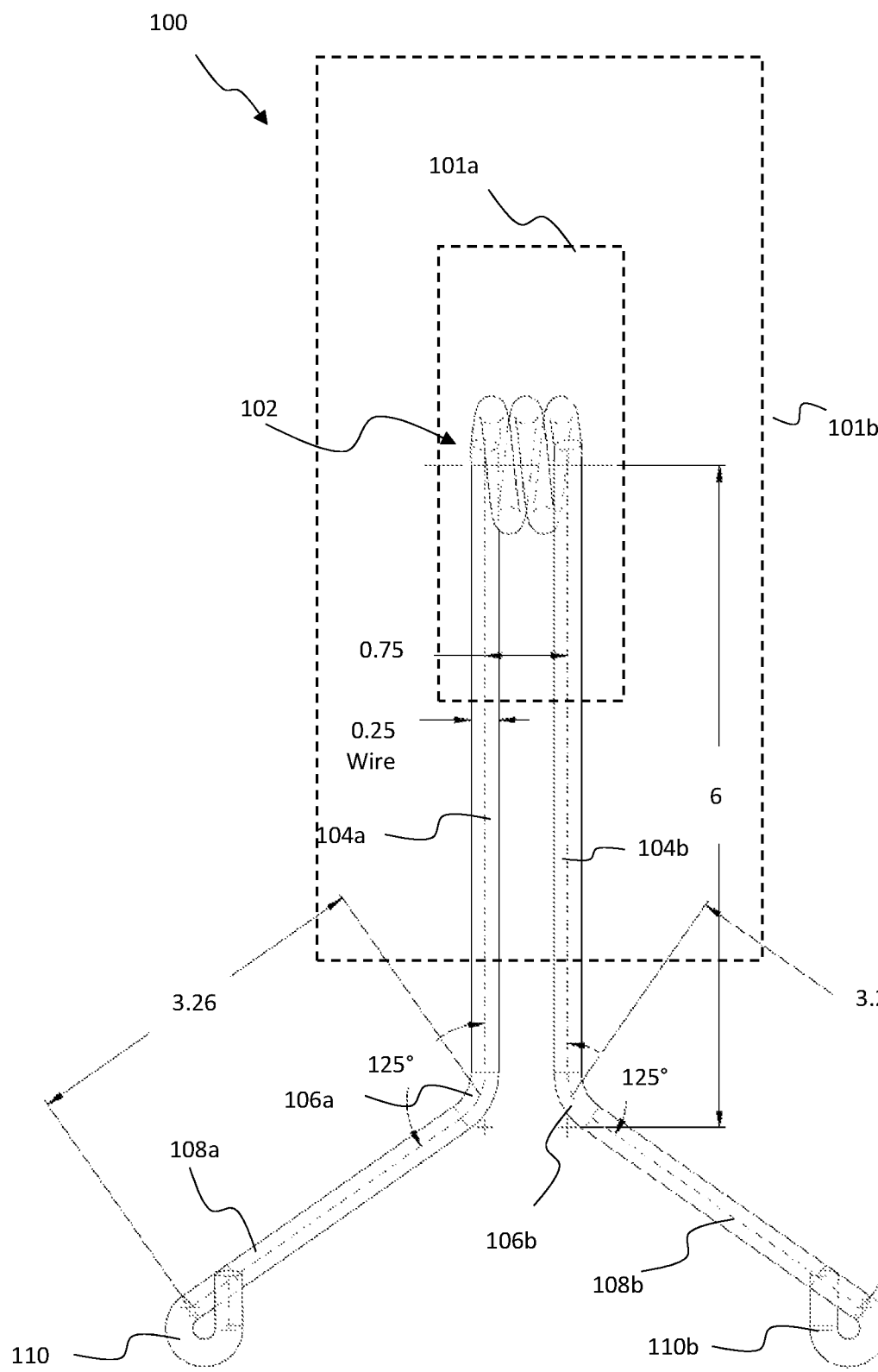
FIG. 8 is a front view of an embodiment of the present invention.

As depicted in FIGS. 7D and 7E, bioabsorbable component 101 may expand to twice the length and 2.67 times the diameter when hydrated. In some embodiments, bioabsorbable component 101 may expand between 1.5 and 3 times in length. In some embodiments, bioabsorbable component 101 may expand between 1.5 and 3 times in diameter. In some embodiments, bioabsorbable component 101 expands in one direction. In some embodiments, bioabsorbable component 101 expands in two directions. In some embodiments, bioabsorbable component 101 expands in all directions.

In an embodiment, non-bioabsorbable component 103 is comprised entirely of a single wire construction. In an embodiment, non-bioabsorbable component 103 is comprised of a single wire construction, wherein the wire has a generally circular cross-section. Starting with a single wire, body section 102, beams 104, spring components 106, anchoring arms 108, and scaffoldings 110 can be constructed by bending the wire into the desired anchoring orientation. Using a single wire construction greatly reduces the manufacturing time, costs, and complexities.

In some embodiments, biopsy marker 100 has a total length in the longitudinal direction between about 1 mm and 20 mm when in a dehydrated state. In some embodiments, the length of biopsy marker 100 is between 7.5 mm and 10 mm when dehydrated. In some embodiments, biopsy marker 100 has a length of 5 mm when dehydrated and an outer diameter of 1.3 mm when dehydrated. In some embodiments, non-bioabsorbable component 103 has a total length in the longitudinal direction between about 1 mm and 7 mm.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all the generic and specific features of the invention herein described, and all statements of the scope of the invention that, as a matter of language, might be said to fall therebetween.

What is claimed is:

1. A biopsy marker, comprising:
  a bioabsorbable component;
  a non-bioabsorbable component, the non-bioabsorbable component including:
    a body section having a predefined non-linear shape, wherein the body section resides at least partially within the bioabsorbable component;
    a first beam extending from the body section to a first spring component;
    the first spring component residing between a first anchoring arm and the first beam;
    an insertion orientation and an anchoring orientation, the insertion orientation including the biopsy marker having a lateral span that is different than the lateral span of the biopsy marker when in the anchoring orientation;
    the insertion orientation including the first anchoring arm subject to an external force to overcome a spring force from the first spring component; and
    the anchoring orientation including the first anchoring arm being free of the external force and the first spring component causing the first anchoring arm to move into a different orientation thereby changing the lateral span of the biopsy marker.

2. The biopsy marker of claim 1, further including a non-linear scaffolding section at a distal end of the first anchoring arm.

3. The biopsy marker of claim 2, wherein the scaffolding section includes a j-hook or a barb-like feature.

4. The biopsy marker of claim 1, wherein the body section has a coil-shape.

5. The biopsy marker of claim 1, wherein the first spring component is a torsion spring.

6. The biopsy marker of claim 1, wherein the first spring component is an elbow spring.

7. The biopsy marker of claim 1, wherein the non-bioabsorbable component is made from a metallic material.

8. The biopsy marker of claim 1, wherein the non-bioabsorbable component is comprised of a single continuous wire.

9. The biopsy marker of claim 1, further including the bioabsorbable component comprised of an expandable material that can be dehydrated to reduce its size and hydrated to increase its size.

10. The biopsy marker of claim 9, further including:
the body section residing within the bioabsorbable component when the bioabsorbable component is in a dehydrated state;
the first beam having a length greater than a distance between the body section and an outer surface of the bioabsorbable component when in the dehydrated state, such that the first spring component resides outside of the bioabsorbable component when in the dehydrated state.

11. The biopsy marker of claim 1, further including:
a second beam extending from the body section to a second spring component;
the second spring component residing between a second anchoring arm and the second beam;
the insertion orientation further including the second anchoring arm being subject to a force to overcome the spring force from the second spring component; and
the anchoring orientation further including the second anchoring arm being free of the force and the second spring component causing the second anchoring arm to move into a different orientation thereby changing the lateral span area of the biopsy marker.

12. A biopsy marker, comprising:
a bioabsorbable component, wherein the bioabsorbable component can be dehydrated to reduce its size and hydrated to increase its size;
a non-bioabsorbable component comprised of a single wire, the non-bioabsorbable component including:
a body section having a predefined non-linear shape, wherein the body section resides at least partially within the bioabsorbable component;
a first beam extending from the body section to a first spring component;
the first spring component residing between a first anchoring arm and the first beam;
an insertion orientation and an anchoring orientation, the insertion orientation including the biopsy marker having a lateral span that is different than the lateral span of the biopsy marker when in the anchoring orientation;
the insertion orientation including the first anchoring arm subject to an external force to overcome a spring force from the first spring component; and
the anchoring orientation including the first anchoring arm being free of the external force and the first spring component causing the first anchoring arm to move into a different orientation thereby changing the lateral span of the biopsy marker.

13. The biopsy marker of claim 12, further including a non-linear scaffolding section at a distal end of the first anchoring arm.

14. The biopsy marker of claim 12, wherein the body section has a coil-shape.

15. The biopsy marker of claim 12, wherein the first spring component is a torsion spring.

16. The biopsy marker of claim 12, wherein the first spring component is an elbow spring.

17. The biopsy marker of claim 12, further including:
the body section residing within the bioabsorbable component when the bioabsorbable component is in a dehydrated state;
the first beam having a length greater than a distance between the body section and an outer surface of the bioabsorbable component when in the dehydrated state, such that the first spring component resides outside of the bioabsorbable component when in the dehydrated state.

18. The biopsy marker of claim 12, further including:
a second spring component residing between a second anchoring arm and the body section;
the insertion orientation further including the second anchoring arm being subject to an external force to overcome the spring force from the second spring component; and
the anchoring orientation further including the second anchoring arm being free of the external force and the second spring component causing the second anchoring arm to move into a different orientation thereby changing the lateral span of the biopsy marker.

19. A biopsy marker, comprising:
a non-bioabsorbable component, wherein the non-bioabsorbable component includes:
a body section having a predefined non-linear shape;
a first beam extending from the body section to a first spring component;
the first spring component residing between a first anchoring arm and the first beam;
a second beam extending from the body section to a second spring component;
the second spring component residing between a second anchoring arm and the second beam;
an insertion orientation and an anchoring orientation, the insertion orientation including the biopsy marker having a lateral span that is different than the lateral span of the biopsy marker when in the anchoring orientation;
the insertion orientation including the first anchoring arm subject to an external force to overcome a spring force from the first spring component and the second anchoring arm subject to the external force to overcome a spring force from the second spring component; and
the anchoring orientation including the first and second anchoring arms being free of the external force and the first and second spring components respectively causing the first and second anchoring arm to move into a different orientation thereby changing the lateral span of the biopsy marker;
a bioabsorbable component, wherein the bioabsorbable component can be dehydrated to reduce its size and hydrated to increase its size;

the body section residing within the bioabsorbable component when the bioabsorbable component is in a dehydrated state;

the first beam having a length greater than a distance between the body section and an outer surface of the bioabsorbable component when in the dehydrated state, such that the first spring component resides outside of the bioabsorbable component when in the dehydrated state; and the second beam having a length greater than a distance between the body section and an outer surface of the bioabsorbable component when in the dehydrated state, such that the second spring component resides outside of the bioabsorbable component when in the dehydrated state.

* * * * *